United States Patent [19]

de Greef et al.

[11] Patent Number: 4,520,809

[45] Date of Patent: Jun. 4, 1985

[54] ANAESTHETIC INDUCTION DEVICE

[76] Inventors: Magdel N. de Greef, 13 Nederburgh St., Welgemoed, Bellville, Cape Province; Ian D. Smit, 26 Campbell St., Observatory, Cape Town, Cape Province, both of South Africa

[21] Appl. No.: 457,258

[22] Filed: Jan. 12, 1983

[30] Foreign Application Priority Data

Jan. 12, 1982 [ZA] South Africa ............... 82/0183
Oct. 11, 1982 [ZA] South Africa ............... 82/7424

[51] Int. Cl.³ .................................. A61M 15/00
[52] U.S. Cl. .................... 128/200.24; 128/150; 128/207.18
[58] Field of Search ............ 128/200.24, 200.28, 128/203.12, 150, 774, 728, 204.18, 206.29; 604/77, 54; 215/11 B

[56] References Cited

U.S. PATENT DOCUMENTS

| 196,594 | 10/1877 | Patch | 128/150 |
|---|---|---|---|
| 411,794 | 10/1889 | Eggers | 215/11 B |
| 941,905 | 11/1909 | Bajon | 604/77 |
| 2,521,084 | 9/1950 | Oberto | |
| 3,020,911 | 5/1960 | Girden | |
| 3,037,501 | 6/1962 | Miller | |
| 3,091,236 | 5/1963 | Delbert | 128/206.29 |
| 3,895,533 | 7/1975 | Steier | 128/774 |
| 4,216,769 | 8/1980 | Grimes | 128/207.13 |
| 4,381,773 | 5/1983 | Goodnow et al. | 604/54 |

FOREIGN PATENT DOCUMENTS

| 125962 | 3/1960 | New Zealand . |
|---|---|---|
| 154169 | 4/1969 | New Zealand . |
| 254945 | 5/1948 | Switzerland . |
| 713437 | of 0000 | United Kingdom . |
| 788905 | of 0000 | United Kingdom . |
| 2081105 | 2/1982 | United Kingdom . |

Primary Examiner—Henry J. Recla
Attorney, Agent, or Firm—Lewis H. Eslinger

[57] ABSTRACT

A gas induction device 10 suitable for use in anaesthetizing a child comprises means 12 defining an outlet opening 14 and a flow passage 16 for gases leading to the outlet opening, and an artificial teat 18 connected to said means. The teat can be hollow and can contain a suitable medication 30 which is then sucked from the teat prior to or during the initial stages of anaesthesia.

4 Claims, 4 Drawing Figures 4,520,809

ANAESTHETIC INDUCTION DEVICE

BACKGROUND OF THE INVENTION

This invention relates to a gas induction device. More particulary it relates to a gas induction device suitable for use in anaesthetizing a child.

Present-day techniques of inducing anaesthesia in small children include intravenous or intramuscular injection of drugs, rectal administration of drugs, gaseous induction of anaesthesia with gas or vapour via the respiratory tracts, or a combination of any two or more of these techniques. All of these techniques suffer from certain disadvantages. With the gaseous induction technique, the child usually needs a lot of pre-operative sedative medicine to quieten it before the anaesthetist is able to approach it with the gas delivery system. The gas delivery system usually comprises a black, and to the child unfamiliar and fear-inducing, mask, which needs to be held to the child's face. Invariably a struggle develops, resulting in the child holding its breath or starting to scream or cry. Clearly this is not desirable and may even cause psychological harm to the child.

It is an object of the present invention to overcome or at least alleviate the above disadvantages.

SUMMARY OF THE INVENTION

According to the invention there is provided a gas induction device suitable for use in anaesthetizing a child, which device comprises:
  means defining an outlet opening and a flow passage for gases leading to the outlet opening; and
  an artificial teat connected to said means.

The term 'gases' is used in a wide sense so as to include also vapours and other gas-borne substances.

There may be an inlet opening leading into the passage, the inlet opening being substantially smaller than the outlet opening.

Preferably the size and shape of the outlet opening generally corresponds to that of the lower aspect of a child's nose.

The artificial teat may be hollow and may have a perforation at its distal end.

The teat may contain a substance which can be sucked from the teat through the perforation.

The substance may comprise a medication suitable for oral intake by the child prior to or during the initial stages of anaesthesia.

The invention will now be described in more detail, by way of example, with reference to the accompanying drawings.

DETAILED DESCRIPTION OF PREFERRED EMBODIMENT

Figure 1:
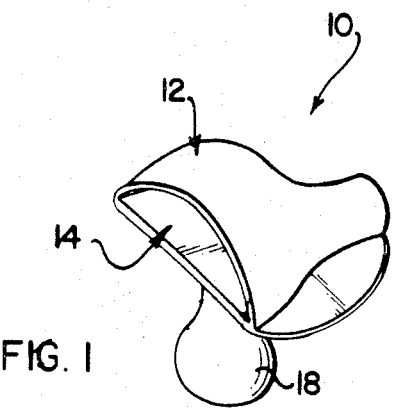
FIG. 1 is a three dimensional view of a gas induction device in accordance with the invention.
Figure 2:
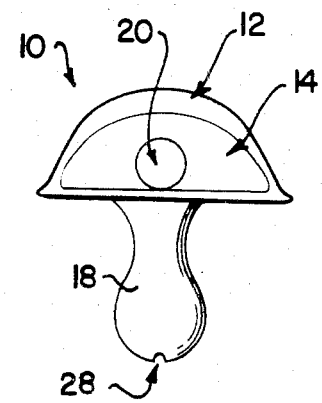
FIG. 2 is an end elevation of the device, seen from the outlet end.
Figure 3:
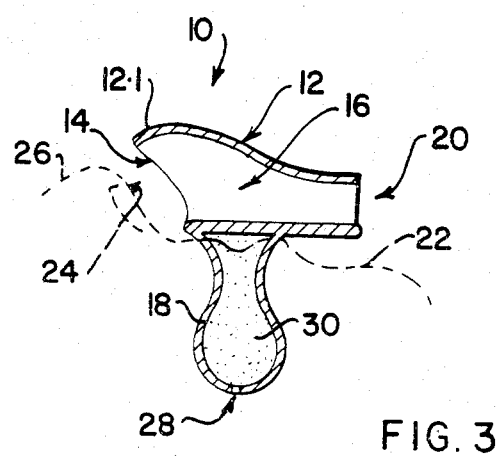
FIG. 3 is a vertical section of the device, being shown in position in a child's mouth.

Referring first to FIGS. 1 to 3 of the drawings, reference numeral 10 generally indicates a gas induction device comprising means 12 defining an outlet opening 14 and a flow passage 16 for anaesthetic gases leading to the outlet opening, and an artifical teat 18 connected to said means.

The teat 18 is of a soft latex rubber or other suitable material. The means 12 may be of the same material as that of the teat 18, although the walls should be thicker than those of the teat so that the means 12 will be sufficiently firm. Alternatively, the means 12 could be of a material which is relatively hard in comparison with the material of the teat 18. There is an inlet opening 20, substantially smaller than the outlet opening, which leads into the passage 16.

When the device is in position in a child's mouth, as shown in FIG. 3 where dotted line 22 indicates the outline of part of the child's face, the outlet opening 14 is in alignment with the lower aspect 24 of the child's nose 26. The shape and size of the outlet opening, as will be seen in FIG. 2, corresponds generally to the shape and size of the lower aspect of the child's nose. As will be seen in FIG. 3, the means 12 has a light overhang 12.1 at the outlet opening and is shaped to direct anaesthetic gases flowing from the outlet opening towards the child's nostrils. This is to minimise the escape of anaesthetic gases through the gap between the outlet opening 14 and the child's nose.

The teat 18 is hollow, has a perforation 28 at its distal end, and contains a medication 30 suitable for oral intake by the child prior to or during the initial stages of anaesthesia. The medication 30 may contain a tranquilliser, analgesic or other suitable pre-medication substance and may be prepackaged in the teat 18. If desired, the medication 30 may be sealed hermetically in the teat by means of a wax plug or a peel-off covering closing the perforation 28.

Figure 4:
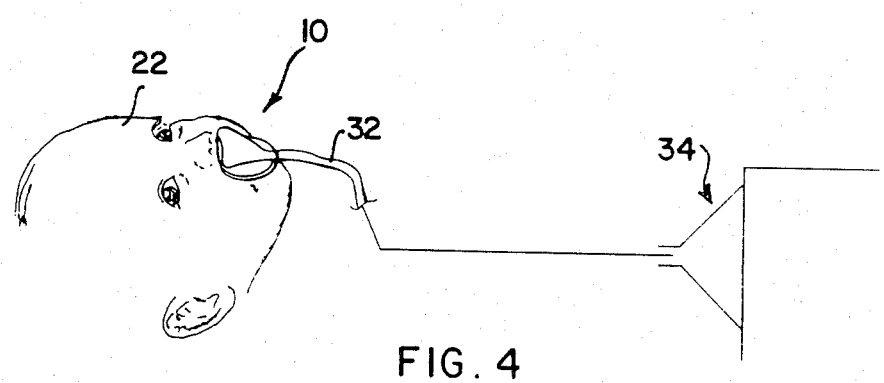
FIG. 4 illustrates schematically how the device is used.

Referring now to FIG. 4, it will be seen that the device 10 is connected via a flexible tube 32 to apparatus 34 for providing anaesthetic gases. The tube 32 may be connected to the device 10 by the tube having a tapered end which fits tightly in the opening 20. If desired, gripe water, honey, or some other palatable substance may be applied to the outside of the teat 18 prior to insertion into the child's mouth. The child will then be able to suck the medication 30 slowly from the teat, whereafter the flow of anaesthetic gases through the tube 32 and the passage 16 can slowly be turned on, thereby gently anaesthetizing the child to the first stages of anaesthesia. In this way, the child can be rendered insensible within two to three minutes without a struggle. Thereafter, the device 10 can be removed and further anaesthetic gases administered by means of the usual mask.

To prevent misalignment of the device 10, the means 12 may be shaped to engage with the sides of the child's nose. Alternatively, or in addition, the teat 18 may be somewhat flattened or oval in cross section or have wing formations along its sides. This is not shown in the drawings.

If desired, the tube 32 may be formed integrally with the device 10.

What we claim is:

1. A gas induction device for use in anaesthetizing a child, which device comprises:
  gas delivery and directing means having a flared terminal portion which defines an outlet opening adapted to be positioned in close proximity to the child's nostrils and a widening gas flow passage leading to the outlet opening, said gas delivery and directing means including means for fluidically communicating said gas flow passage with an external source of anaesthetizing gas and being shaped and dimensioned to lie over the child's face except for the child's nostrils; and an artificial teat connected to said gas delivery and directing means in such a manner that, when the teat is located in a sucking position in the child's mouth, said gas delivery and directing means is thereby located so that the outlet opening is in close proximity to the child's nostrils, whereby gases flowing through the passage to the outlet opening are delivered from the outlet opening and directed towards the nostrils.

2. A gas induction device according to claim 1, wherein there is an inlet opening leading into the passage, the inlet opening being substantially smaller than the outlet opening.

3. A gas induction device according to claim 1, wherein the artificial teat is hollow and has a perforation at its distal end.

4. A gas induction device according to claim 3, wherein the teat contains a substance which can be sucked from the teat through the perforation, the substance comprising a medication suitable for oral intake prior to or during the initial stages of anaesthesia.

* * * * *